(12) United States Patent
Ouchi

(10) Patent No.: US 7,963,168 B2
(45) Date of Patent: Jun. 21, 2011

(54) INSPECTION APPARATUS AND INSPECTION METHOD USING ELECTROMAGNETIC WAVE

(75) Inventor: Toshihiko Ouchi, Sagamihara (JP)

(73) Assignee: Canon Kabushiki Kaisha, Tokyo (JP)

( * ) Notice: Subject to any disclaimer, the term of this patent is extended or adjusted under 35 U.S.C. 154(b) by 427 days.

(21) Appl. No.: 12/196,084

(22) Filed: Aug. 21, 2008

(65) Prior Publication Data

US 2009/0056455 A1 Mar. 5, 2009

(30) Foreign Application Priority Data

Aug. 31, 2007 (JP) ................. 2007-224940

(51) Int. Cl.
*G01N 21/31* (2006.01)
*G01J 1/42* (2006.01)
(52) U.S. Cl. ........................................ 73/643
(58) Field of Classification Search ............... 73/643
See application file for complete search history.

(56) References Cited

U.S. PATENT DOCUMENTS

| | | | |
|---|---|---|---|
| 5,586,131 A | 12/1996 | Ono et al. | |
| 5,659,560 A | 8/1997 | Ouchi et al. | |
| 5,699,373 A | 12/1997 | Uchida et al. | |
| 5,764,670 A | 6/1998 | Ouchi | |
| 6,854,901 B1 | 2/2005 | Ouchi | |
| 6,909,094 B2* | 6/2005 | Tran et al. | 250/341.1 |
| 6,909,095 B2* | 6/2005 | Tran et al. | 250/341.1 |
| 7,062,116 B2 | 6/2006 | Ouchi | |
| 7,248,995 B2 | 7/2007 | Itsuji et al. | |
| 7,386,024 B2 | 6/2008 | Sekiguchi et al. | |
| 2004/0065831 A1* | 4/2004 | Federici et al. | 250/341.1 |
| 2004/0155192 A1* | 8/2004 | Tran et al. | 250/341.1 |
| 2006/0085160 A1 | 4/2006 | Ouchi | |
| 2006/0111619 A1* | 5/2006 | Castiglione et al. | 600/300 |
| 2006/0197021 A1 | 9/2006 | Ouchi | |

(Continued)

FOREIGN PATENT DOCUMENTS

JP 2004-340763 A 12/2004

(Continued)

OTHER PUBLICATIONS

U.S. Appl. No. 12/196,224, filed Aug. 21, 2008, Applicant: Kousuke Kajiki, et al.

(Continued)

*Primary Examiner* — Hezron Williams
*Assistant Examiner* — Rose M Miller
(74) *Attorney, Agent, or Firm* — Fitzpatrick, Cella, Harper & Scinto

(57) ABSTRACT

The present invention is to provide inspection apparatus and method of being able to acquire electromagnetic wave response information of an inspection object at high speed as average information using an electromagnetic wave. An inspection apparatus using an electromagnetic wave 2 includes an electromagnetic wave generation and irradiation unit 9 which generates an electromagnetic wave and irradiates the electromagnetic wave on an inspection object 11, and an electromagnetic wave detection unit 10 having a plurality of detection units. The plurality of detection units is arranged so as to detect the electromagnetic wave which is irradiated by the electromagnetic wave generation and irradiation unit and is transmitted or reflected with interacting with different sites of the inspection object 11, and is constructed so as to detect the electromagnetic wave from the different sites in different detection time or detection frequencies respectively. The inspection apparatus acquires electromagnetic wave response information on the inspection object 11 based on detection signals from the plurality of detection units.

14 Claims, 7 Drawing Sheets

U.S. PATENT DOCUMENTS

| | | |
|---|---|---|
| 2006/0214176 A1 | 9/2006 | Ouchi et al. |
| 2006/0227340 A1 | 10/2006 | Shioda et al. |
| 2006/0237650 A1 | 10/2006 | Taday |
| 2006/0244629 A1 | 11/2006 | Miyazaki et al. |
| 2007/0029483 A1* | 2/2007 | James et al. ............... 250/336.1 |
| 2007/0030115 A1 | 2/2007 | Itsuji et al. |
| 2007/0158571 A1* | 7/2007 | Cole et al. .................. 250/341.8 |
| 2007/0195921 A1 | 8/2007 | Ouchi |
| 2007/0215808 A1 | 9/2007 | Sekiguchi et al. |
| 2007/0229094 A1 | 10/2007 | Kasai et al. |
| 2007/0235718 A1 | 10/2007 | Kasai et al. |
| 2007/0252604 A1 | 11/2007 | Ouchi et al. |
| 2008/0048792 A1 | 2/2008 | Ouchi et al. |
| 2008/0156991 A1* | 7/2008 | Hu et al. ..................... 250/341.1 |
| 2008/0179526 A1* | 7/2008 | Xu et al. .................. 250/339.07 |
| 2008/0231384 A1 | 9/2008 | Sekiguchi et al. |

FOREIGN PATENT DOCUMENTS

| | | |
|---|---|---|
| JP | 2006-526774 A | 11/2006 |

OTHER PUBLICATIONS

U.S. Appl. No. 12/300,791, filed Nov. 13, 2008, Applicant: Shintaro Kasai, et al.

U.S. Appl. No. 12/091,393, filed Apr. 24, 2008, Applicant: Ryota Sekiguchi, et al.

U.S. Appl. No. 11/632,958, filed Jan. 19, 2007, Applicant: Toshihiko Ouchi, et al.

Takashi Yasuda, et al., Real-Time Two-Dimensional Terahertz Tomography Of Moving Objects, Optics Communications, Nov. 2006, pp. 128-136, vol. 267, Issue 1.

Chinese Office Action dated Nov. 5, 2010 in corresponding Chinese Application No. 200810212465.8.

* cited by examiner

INSPECTION APPARATUS AND INSPECTION METHOD USING ELECTROMAGNETIC WAVE

BACKGROUND OF THE INVENTION

1. Field of the Invention

The present invention relates to an inspection apparatus, an inspection method, and the like which acquire information on a character and the like of a specimen using an electromagnetic wave. In particular, the present invention relates to an inspection apparatus, an inspection method, and the like which acquire information on an object character and the like using an electromagnetic wave in a frequency domain from a millimeter wave band to a terahertz band (30 GHz to 30 THz).

2. Related Background Art

Nondestructive sensing techniques using an electromagnetic wave in a frequency domain from a millimeter wave band to a terahertz band (30 GHz to 30 THz) (hereafter, it is simply called a terahertz (THz) wave) have been developed. Imaging using an electromagnetic wave in a frequency domain of a terahertz band has been developed, and has received attention as a safe see-through inspection apparatus which replaces X-rays. In addition, a spectroscopic technique which finds an absorption spectrum inside a substance and a complex dielectric constant using an electromagnetic wave which has a frequency domain in a terahertz band, and investigates physical properties, such as a bonding state, an analysis technique of a biomolecule, a technique of evaluating a carrier density and mobility, and the like have been developed.

The above-mentioned techniques are applied to defect/contamination inspections of moldings, component/contamination/defect inspections in chemical substances, and the like, and it is studied to use them for nondestructive quality checks in production lines of works. As their objects, in the case of chemical substances, ink, such as a pigment/dyestuff, toner, drugs, cosmetics, paints, and the like are conceivable. On the other hand, an inspection apparatus of drugs using a THz time domain spectrum analysis (Time domain Spectroscopy: TDS) method is proposed (Japanese Patent Application Laid-Open No. 2006-526774). This document expresses that an analysis of a type of internal drugs, and the like can be performed from a surface according to spectral information in a THz wave domain.

A conventional THz-TDS apparatus acquires data with scanning time delay between pump light and probe light. Therefore, typically, tens of seconds to several minutes are required so as to conduct a componential analysis in a 1-mm area. It is necessary to conduct an inspection in an actual factory production line at high speed. Therefore, a conventional THz-TDS apparatus cannot be applied to a total inspection in a factory production line.

On the other hand, the following technique has been studied in a coating inspection apparatus (Optics Communications, Volume 267, Issue 1.1 November 2006, Pages 128-136). The THz-TDS of the article widens a beam of a THz wave in a line, not in a spot, to acquire information on a large area simultaneously, and in consequence, acquires data from a two-dimensional domain at high speed. Furthermore, the THz-TDS acquires the terahertz wave two-dimensionally using an electrooptical crystal, and makes incident angles of the terahertz wave and an excitation light source differed on a surface of the electrooptical crystal to make delay time change locationally. In this way, the THz-TDS can acquire the information without scanning in a delay stage.

However, in a system using the above-mentioned linear beam, an electrooptical crystal which detects a terahertz wave two-dimensionally is indispensable. In that case, in order to compensate low conversion efficiency, a titanium sapphire laser is required as a large output excitation light source, and hence, the system becomes large-sized and expensive. In addition, although this system is to obtain spectral information in each point, inspection speed is not enough to use this system for a total inspection in a factory.

In the production line of a factory, there may be no large difference in an electromagnetic wave response every part of a finished product. When the line has been working over a long time in such a case, so long as it is possible to inspect fluctuations of an electromagnetic wave response in a certain amount of time, it is enough for operation and maintenance of the production line, or quality maintenance of finished products. For example, when pharmaceutical preparations of drugs are produced at high speed, so long as it is possible to acquire an average composition of the pharmaceutical preparations of tens to thousands tablets at high speed, it is possible to treat pharmaceutical preparations in a lot in which abnormality arises. It is also possible to feed it back to a production apparatus to return manufacturing conditions to a normal state in connection with it.

SUMMARY OF THE INVENTION

An inspection apparatus using an electromagnetic wave according to the present invention includes an electromagnetic wave generation and irradiation unit which generates an electromagnetic wave and irradiates the electromagnetic wave on an inspection object, and an electromagnetic wave detection unit having a plurality of detection units. The plurality of detection units is arranged so as to detect the electromagnetic wave which is irradiated by the electromagnetic wave generation and irradiation unit and is transmitted or reflected with interacting with different sites of an inspection object, and is constructed so as to detect the electromagnetic wave from the different sites in different detection time or detection frequencies respectively. By such construction, the inspection apparatus of the present invention acquires electromagnetic wave response information on the inspection object based on detection signals from the plurality of detection units.

In addition, in view of the above-mentioned problems, an inspection method using an electromagnetic wave according to the present invention includes at least the following first to third steps. At a first step, an electromagnetic wave is generated and is irradiated on different sites of an inspection object. At a second step, a plurality of detection units detects the electromagnetic wave, which is transmitted or reflected with interacting with different sites of an inspection object, in different detection time or detection frequencies, respectively. At a third step, electromagnetic wave response information on the inspection object is acquired based on detection signals from the plurality of detection units.

Furthermore, another inspection apparatus for performing an inspection using an electromagnetic wave according to the present invention comprises an electromagnetic wave generation and irradiation unit which generates a terahertz wave and irradiates the terahertz wave on an inspection object, and an electromagnetic wave detection unit having a plurality of detection units, wherein the plurality of detection units are arranged so as to detect a terahertz wave which is irradiated by the electromagnetic wave generation and irradiation unit and is transmitted or reflected with interacting with different sites of an inspection object, and is constructed so as to detect the terahertz wave from the different sites in different detection time or detection frequencies respectively to acquire terahertz wave response information from the inspection object based on detection signals from the plurality of detection units.

Another inspection method for performing an inspection using a terahertz wave according to the present invention is characterized by comprising: a step of generating a terahertz wave and irradiating the terahertz wave on an inspection object; a step of detecting the terahertz wave, which is transmitted or reflected with interacting with different sites of an inspection object, by a plurality of detection units in different detection time or detection frequencies, respectively; and a step of acquiring terahertz wave response information from the inspection object based on detection signals from the plurality of detection units.

In addition, another inspection apparatus for performing an inspection using a terahertz wave comprises: a plurality of generation units for generating a terahertz wave; and a detection unit for detecting the terahertz wave which is generated by the generation unit and is transmitted or reflected by the inspection object, wherein the plurality of detection units is arranged so as to detect the transmitted or reflected terahertz wave with different delay time respectively, and time waveforms of the transmitted or reflected terahertz wave are acquired using the information regarding the terahertz wave which the plurality of detection units detects.

According to the inspection apparatus and method of the present invention, different sites of an inspection object are irradiated with an electromagnetic wave, and the electromagnetic wave which is reflected or transmitted with interacting with these are acquired by a plurality of detection units as signals in different detection time or different frequencies. In consequence, it is possible to obtain the electromagnetic wave response information of the inspection object which is constructed of a plurality of specimens of the same kind or a homogeneous specimen at high speed as average information.

Further features of the present invention will become apparent from the following description of exemplary embodiments with reference to the attached drawings.

DETAILED DESCRIPTION OF THE EMBODIMENTS

Figure 1:
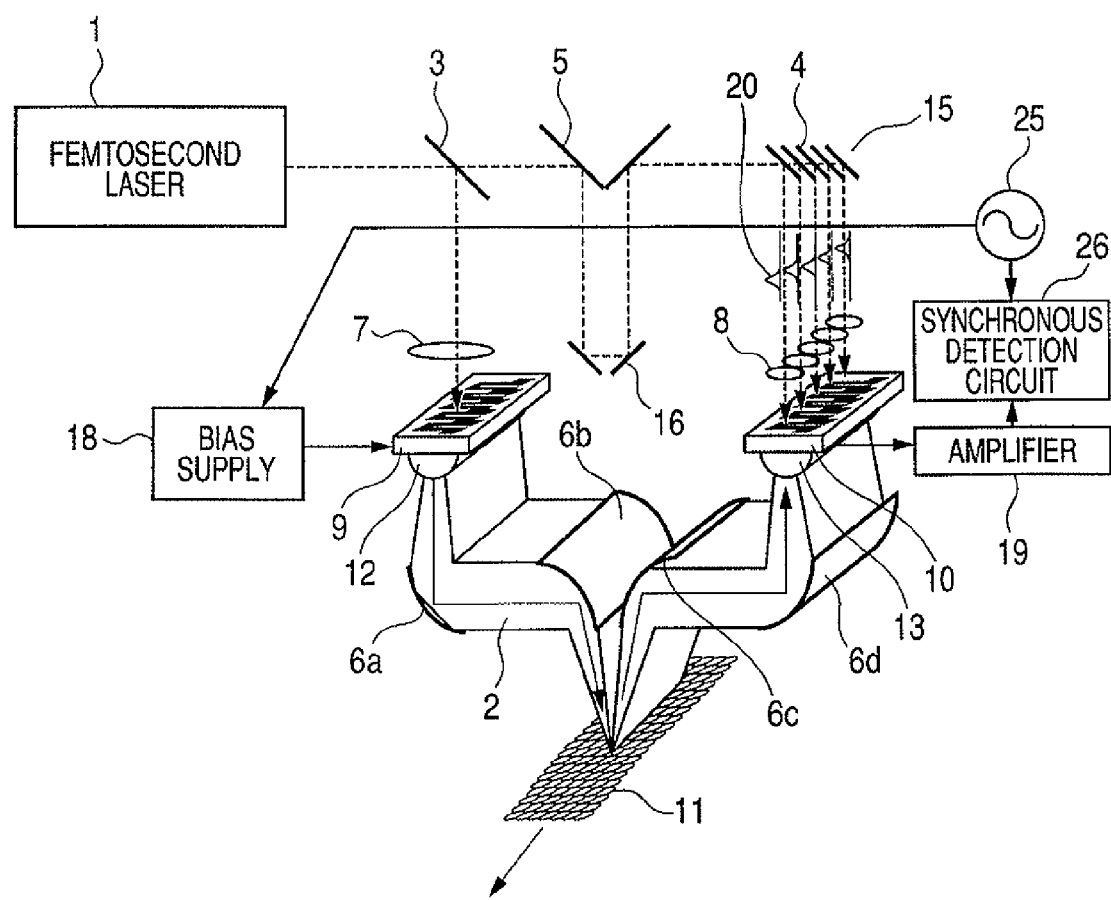
FIG. 1 is a schematic diagram illustrating an inspection apparatus and method relating to an embodiment and a first example according to the present invention.

An embodiment of an inspection apparatus and method according to the present invention will be described with referring to FIG. 1.

In this embodiment, an inspection object which is constructed of a plurality of specimens 11 of the same kind is placed on a belt conveyer or the like, which is a specimen holding unit, and flows and moves with width. In order to inspect an average character of the plurality of whole specimens 11, a terahertz wave 2 is shaped so as to become a broad rectangular beam instead of a usual circular beam, as a propagation path expresses. Then, the beam is condensed and is irradiated on the inspection object, which is constructed of the plurality of specimens 11, in a line, and the terahertz wave reflected from there is detected by a photoconductive device 10, which is an electromagnetic wave detection unit which has a plurality of detection units, as a linear beam.

A laser beam from a femtosecond laser 1 is divided into two optical paths by a half-mirror 3, and one side of them is irradiated on a photoconductive device 9 which is an electromagnetic wave generation and irradiation unit. The photoconductive device 9 is constructed by arranging elements in the shape of a one-dimensional array as illustrated in FIG. 1. The laser beam is made into a rectangular beam to be irradiated over the whole array elements of the photoconductive device 9 with a lens 7 simultaneously. A bias supply 18 supplies a voltage, modulated by a signal of a pulse generator 25, to all the electrodes of the array elements of the photoconductive device 9. Typically, a 5-kHz and ±10V signal is given to all the electrodes of the array elements.

A laser beam with 30 mW of power is irradiated over a full area of the photoconductive device 9, and terahertz wave pulses generated from the photoconductive device 9 is irradiated on the plurality of specimens 11 through a silicon (Si) semi-cylindrical lens 12 and parabolic cylinder surface mirrors 6a and 6b. The terahertz wave pulses reflected by the plurality of specimens 11 are incident into the photoconductive device 10 for detection through parabolic cylinder surface mirrors 6c and 6d, and Si semicircular pillar lens 13. The photoconductive device 10 which is an electromagnetic wave detection unit is arranges in the shape of a one-dimensional array. A signal from each element is independently acquirable through amplifiers 19, which are constructed in parallel, and synchronous detection circuits 26. Each of the synchronous detection circuits 26 performs synchronous detection of the signal from each of the amplifiers 19 using a signal of the pulse generator 25. It is possible to detect the terahertz wave in the photoconductive device 10 by irradiating the laser beam, branched by the half-mirror 3 as probe light, on each detection unit of the photoconductive device 10 with preparing a predetermined period difference. Thereby, the plurality of detection units of the photoconductive device 10 detects the electromagnetic wave from the plurality of specimens 11 in different detection time respectively.

In adjusting the time difference, delay time is usually changed by scanning an optical delay device 16, and a time waveform of a terahertz wave is acquired. However, in that case, as described in a description location of the problems mentioned above, waveform acquisition takes time.

Then, in this embodiment, a pulse which gives delay time (detection time) which is different as denoted by reference numeral 20 is entered through a lens 8 every element of the photoconductive device 10 in the one dimensional array. Thereby, it is possible to acquire a signal in each delay time in parallel regarding the signal acquired independently. In order to attain this, it is made for delay time to differ little by little by a plurality of branching mirrors 4, and a total reflection mirror 15 is used only in the last stage. Although a five-element array is constructed in FIG. 1, actually, in order to enhance time resolution, it is desirable to provide ten or more elements.

Figure 2:
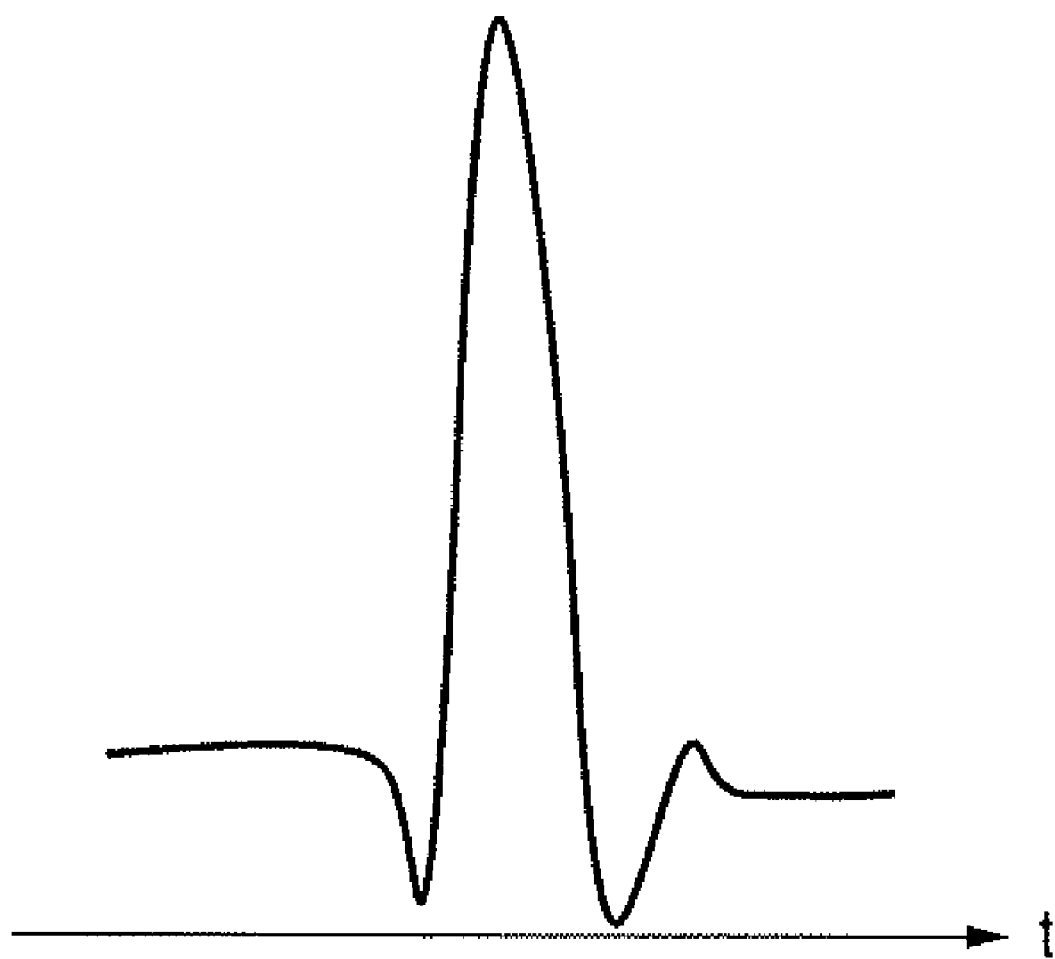
FIG. 2 is an explanatory chart of an example of an acquired waveform of a THz signal.

FIG. 2 illustrates an example of a time waveform acquired in the above-mentioned parallel processing type construction. Here, an example of using a 10-element array is illustrated. In FIG. 2, a THz time waveform is obtained by synthesizing measured values (1) to (10) corresponding to time of respective gray strap portions. Actually, when it is not possible to slim a time pitch finely enough only by the photoconductive device 10 in the one-dimensional array spatially, it is also good to use a delay device 16 including a reflective mirror 5 and a Littrow reflector. For example, when the time delay which is equivalent to 3 psec is scanned with the delay device 16 when the time pitch of fixed delay time is 3 psec, it is possible to obtain a smooth time waveform. Even in such construction, it is possible to increase waveform acquisition speed remarkably in comparison with a case of performing time scanning of 30 or more psec.

In the inspection apparatus or method using an electromagnetic wave according to the present invention, a plurality of detection units of an electromagnetic wave detection unit is arranged so as to detect the electromagnetic wave which is irradiated by the electromagnetic wave generation and irradiation unit and is transmitted or reflected with interacting with different sites of an inspection object. In addition, in the above-mentioned embodiment, the plurality of detection units is constructed so as to detect the electromagnetic wave from the different sites in different detection time or detection frequencies respectively to acquire average electromagnetic wave spectral information which is information on an electromagnetic wave response of the inspection object based on detection signals from the plurality of detection units.

In another embodiment, it is also possible to construct an electromagnetic wave generation and irradiation unit and a plurality of detection units of an electromagnetic wave detection unit so as to detect the electromagnetic wave from the different sites in different detection frequencies, respectively (refer to fourth embodiment mentioned later). The electromagnetic wave may be an electromagnetic wave other than the terahertz wave, and an inspection principle in this case is the same as that of the case of the terahertz wave.

In addition, in the above-mentioned embodiments, an electromagnetic wave is a terahertz wave pulse including some frequency components of a frequency domain of 30 GHz to 30 THz. Nevertheless, it is also possible to adopt construction that an electromagnetic wave includes a plurality of frequency components in a frequency domain of 30 GHz to 30 THz and the plurality of frequency components is irradiated on different sites of an inspection object respectively (refer to the below-mentioned fourth embodiment).

Furthermore, in the above-mentioned embodiments, the information on an electromagnetic wave response is based on detection signals from sites of a plurality of different specimens of an inspection object in which a plurality of specimens of the same kind is arranged in a line. Here, electromagnetic wave response information is obtained by synthesizing the detection signals from the plurality of different specimens, and this is made into average information, including an average character of the specimens, and the like. According to this inspection principle, it is also possible to obtain electromagnetic wave response information based on the detection signals from the different sites of a homogeneous specimen to make this into average information, including an average character of the specimen, and the like.

Moreover, in the above-mentioned embodiment, an inspection object moves, and different sites of the inspection object which are irradiated by one shot of the electromagnetic wave change sequentially as the inspection object moves. At this time, it is also possible to save a plurality of detection signals from each detection unit of the plurality of detection units for fixed time in memory, and to acquire average electromagnetic wave response information based on this. In this case, it is also possible to average first a plurality of detection signals over two or more shots from each detection unit, and to acquire average electromagnetic wave response information by synthesizing these averaged ones. Alternatively, it is also good to first synthesize detection signals in a single shot from respective detection units, and to acquire average electromagnetic wave response information by averaging these synthetic signals over two or more shots.

According to the inspection apparatus and method of this embodiment, an electromagnetic wave is irradiated on an inspection object as a beam having a certain spread, and the electromagnetic wave from this is acquired in a plurality of detection units as signals in different detection time or different frequencies. Hence, it is possible to obtain the electromagnetic wave response information of the inspection object which is constructed of a plurality of specimens of the same kind or a homogeneous specimen at high speed as average information. Thereby, it is possible to acquire a character of this, for example, in a manufacturing process of a material, such as a chemical substance, to inspect at high speed whether it is manufactured normally. In additions it is also possible to perform nondestructively screening of an abnormal lot or feedback control for operation and maintenance of manufacturing conditions of a manufacturing apparatus. Therefore, it becomes possible to maintain quality, to increase productivity, and to reduce cost. In this way, when performing mass-production, it is possible to provide an apparatus and a method of acquiring and inspecting the character of products in a whole line at high speed, and an inspection method and an inspection apparatus for screening products and returning manufacturing conditions to a normal state, using this.

EXAMPLES

Hereafter, more specific examples will be described according to drawings.

Example 1

A first example according to the present invention uses a terahertz time domain spectrum (THz-TDS) apparatus, as illustrated in FIG. 1 mentioned above, as a base. In this example, devices where electrodes are patterned on low-temperature growth gallium arsenide (LT-GaAs) are used as the photoconductive devices 9 and 10. Using the femtosecond laser 1 with a pulse width of 120 fsec and a wavelength of 780 nm, this example irradiates a 30-mW laser beam simultaneously on all the elements of the array of the photoconductive device 9 in a generation side to generate a broad terahertz beam. In this example, the specimen 11 is a drug manufactured at high speed, and moves in an arrow direction.

When being condensed into a line by the parabolic reflector 6b, as shown in FIG. 1, the broad terahertz beam 2 is irradiated on the plurality of tablets 11 simultaneously, and the tablet samples move sequentially also during measurement. Then, the terahertz wave reflected by these tablets includes information on each site of the plurality of specimens irradiated by a linear terahertz wave at an each moment, and when this is processed, it is possible to acquire average information on the specimens 11 of the same kind. Here, although the tablet samples move, even if they are fixed, it is possible to acquire the average information on the specimens 11 of the same kind.

In this example, the photoconductive device 10 in a detection side is constructed of 16 elements, and can attain delay of 30 psec as the whole by each element acquiring a signal every delay of 2 psec pitch. Here, the synchronous detection circuit 26 may be constructed of a digital signal processor (DSP) so as to be able to perform a lot of signal processing.

As an example, a longitudinal length of the broad beam on a sample surface is 10 cm typically at this time, and a space between the photoconductive elements in the detection side in the case of division into 16 pieces becomes about 6 mm. Hence, it is good to make also a space between the half-mirrors 4 be about 6 mm. Nevertheless, such sizes are examples and are not limited to these. In addition, the space between the half-mirrors 4 and the space between the elements of the photoconductive device 10 in the detection side does not necessarily need to be the same, and may be changed by the lens 8, and the like. Namely, in the case of the fixed delay of 2 psec, it corresponds to a distance difference of 0.6 mm when the half-mirrors 4 are in the air, and it is satisfactory to use an optical component (not shown), such as a lens with a magnification of 10, for the space of 0.6 mm between the half-mirrors 4 and the space of 6 mm between the elements of the photoconductive device 10.

Also in this example, the delay device 16 performs time scanning of 2 psec at high speed, and the gray straps (1) to (10) in FIG. 2 describe scan widths in respective time of parallel acquisition of signals. Nevertheless, this scanning by the delay device 16 is not indispensable. In FIG. 2, although the gray strap is divided into ten areas, it is divided into 16 areas actually. As a result, a time waveform as shown in FIG. 2 is obtained, and when this is Fourier-transformed, average components of the plurality of tablets 11 can be analyzed.

Figure 3:
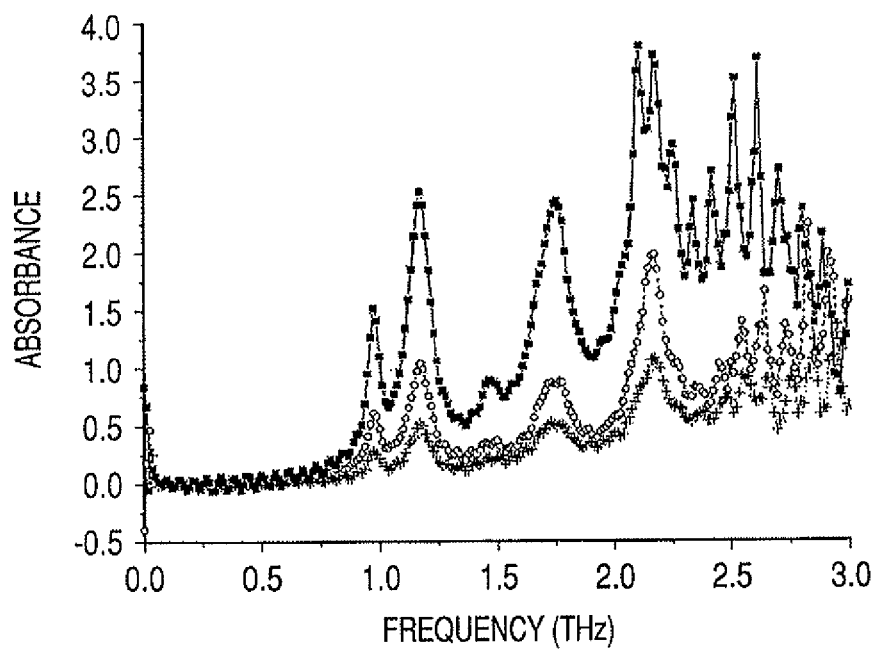
FIG. 3 is an explanatory graph of examples of absorbance spectra of inspection objects.

FIG. 3 illustrates absorbance spectra of cimetidine which is a typical peptic ulcer agent (histamine H2 receptor antagonist). It turns out that a plurality of absorption peaks called characteristic fingerprint spectra are seen. FIG. 3 illustrates measurement examples of absorbance spectra of the tablet samples mixed in weight concentrations of 10% (illustrated by pluses in the figure), 20% (white circles), and 50% (black squares) into polyethylene powder. Pellets in 200 mg were used for this measurement, and 60 times of measurement was performed. There are characteristic peaks in four locations of a: 0.98 THz, b: 1.17 THz, c: 1.73 THz, and d: 2.17 THz.

Fluctuations of a component ratio and polymorphism of a crystal may arise in process of pharmaceutical preparation. Since these have influence on drug effect, a pharmaceutical preparation must be removed by screening when it is out of a reference value. Conventionally, finished products were inspected with a liquid chromatography for presence of occurrence of the crystal polymorphism to be checked by a component ratio, a dissolution rate, and the like. This was a sampling type of destructive inspection, and since an inspection required huge time, it led to a cost increase. In addition, since it was the sampling inspection, when abnormality arose, a lot of pharmaceutical preparations before and behind that needed to be discarded, and productive efficiency also became low.

Figure 4:
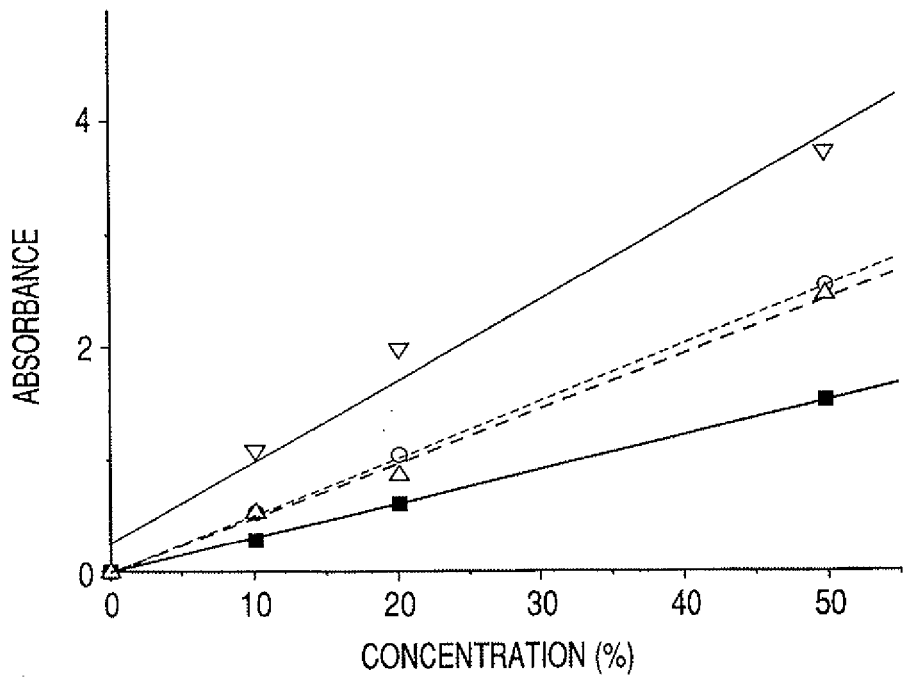
FIG. 4 is a graph illustrating examples of calibration curves of the absorbance in the examples in FIG. 3.

Calibration curves were prepared by plotting respective peaks in the case of cimetidine of the above-mentioned example from the absorbance, as illustrated in FIG. 4. In FIG. 4, black rectangles denote 0.98 THz, white circles do 1.17 THz, white triangles do 1.73 THz, and white reverse triangles do 2.17 THz. The absorbance changes in proportion to the concentration, and hence, the concentration can be calculated from the absorbance according to the Lambert-Beer's law. It is conceivable that a reason why the line does not pass the zero point in 2.17 THz in FIG. 4 is because an error is large in a high concentration region. In addition, this data is derived from the samples for the absorbance measurement, but in actual drugs, not polyethylene but an additive agent used for pharmaceutical preparation, such as magnesium stearate, macrogol, hydro proxy cellulose, or a talc is used.

According to the inspection apparatus or method according to this example, it is possible to acquire information on an average character of a plurality of pharmaceutical preparations which move at high speed. Hence, when a mixing ratio of one or more bulk drugs and additive agents is determined beforehand, it is possible to discriminate from the frequency or absorbance of the above fingerprint spectrum whether they are mixed correctly. Then, when being out of the standard, actions such as removal of pharmaceutical preparations from a movable conveyor and discard are taken, and hence, it is possible to perform a drug inspection nondestructively at high speed.

Figure 5:
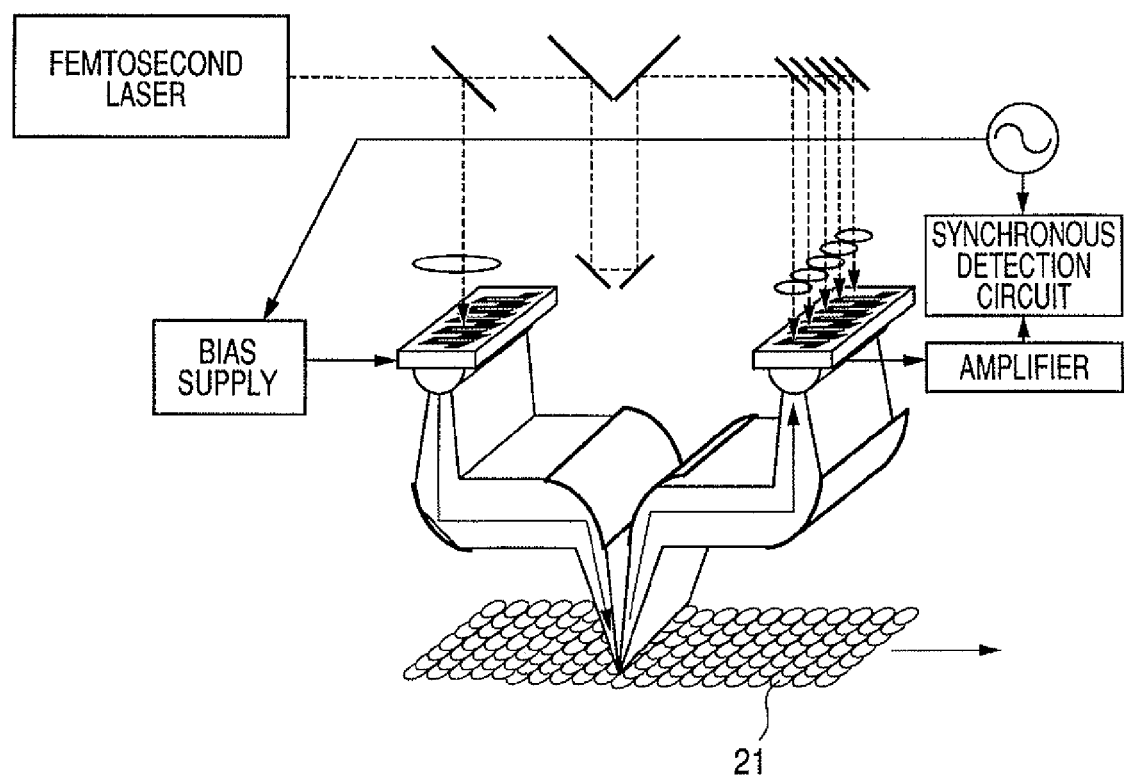
FIG. 5 is a schematic diagram illustrating an example of another electromagnetic wave irradiation method of a first example according to the present invention.

In the example in FIG. 1, a longitudinal direction of a linear beam of a terahertz wave is made parallel to a moving direction of pharmaceutical preparations. Nevertheless, directional relation is not limited to this, but it is also good to allow a full width of pharmaceutical preparations under manufacturing to be irradiated with a terahertz beam by making a longitudinal direction of the beam perpendicular to or slant against a moving direction of the specimens 21 as illustrated in FIG. 5 (reference numerals of the same kind of parts as those in FIG. 1 are omitted). Detection principles are the same.

Figure 8:
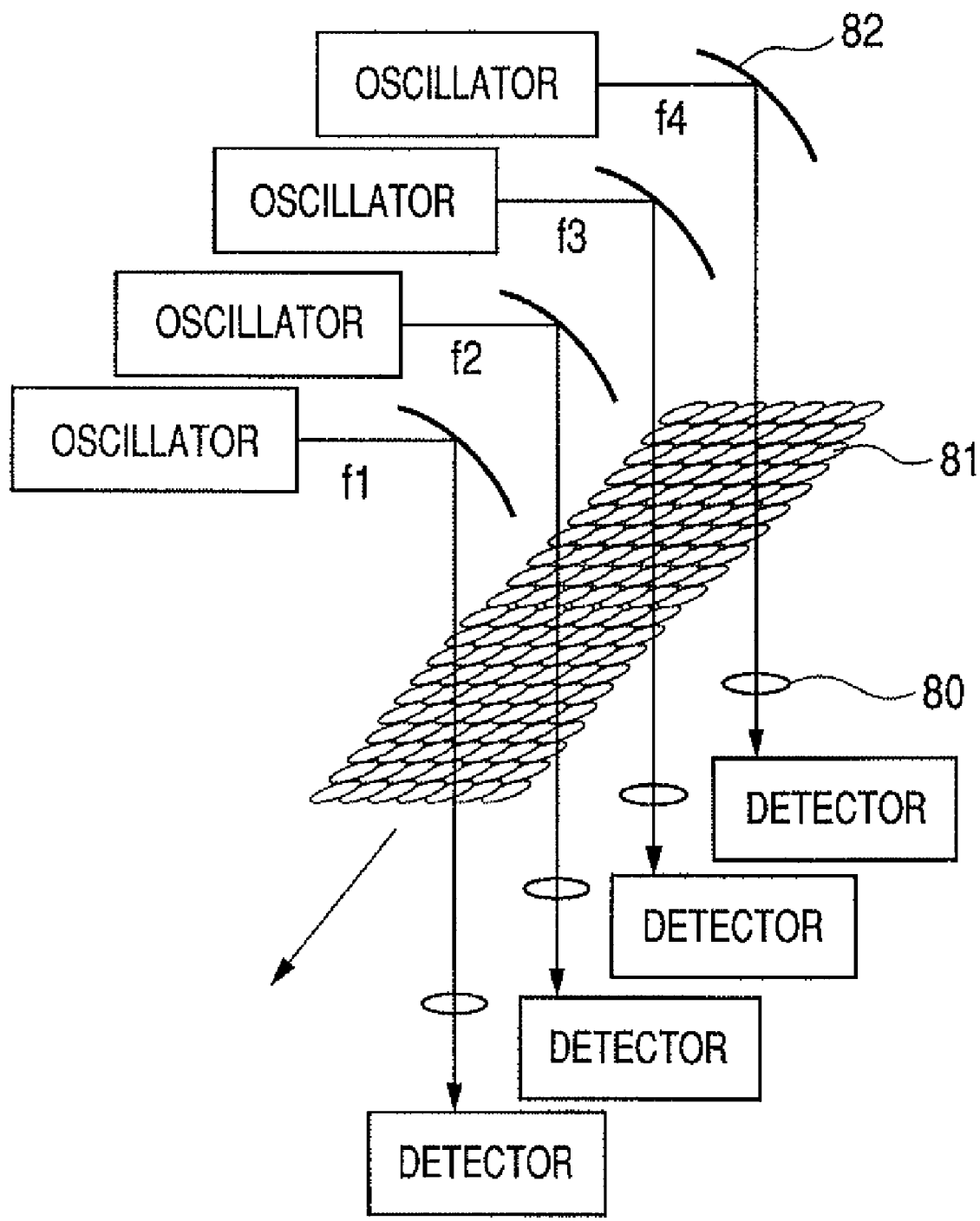
FIG. 8 is a schematic diagram illustrating an inspection apparatus and method relating to a fourth example according to the present invention.

In this example, a photoconductive device was used as a terahertz wave (electromagnetic wave) generation and detection unit. However, electrooptical crystals, such as zinc telluride (ZnTe) and 4-dimethylamino-N-methylstilbazolium-tosylate (DAST), and semiconductor crystals, such as indium arsenide (InAs), and semi insulating gallium arsenide (SI-GaAs) can be used. In addition, although components differ, it is also good to adopt electromagnetic wave transmission arrangement as shown in FIG. 8 or construction by combining transmission and reflection.

In addition, although a drug is exemplified as a specimen which forms an inspection object, the specimen is not limited to this. It is also good to use the inspection apparatus or method of this example in manufacturing processes of ink of pigments/dyestuffs, toner, cosmetics, and paints which are other chemical substances. As long as being a plurality of specimens of the same kind or a homogeneous specimen as a specimen which forms an inspection object, what kind of thing may be used.

According to this example, not only it is possible to acquire a character in a manufacturing process of a material, such as a chemical substance, and to inspect at high speed whether it is normally manufactured, but also it is possible to perform nondestructively screening of an abnormal lot or feedback control for operation and maintenance of manufacturing conditions of a manufacturing apparatus. Therefore, it becomes possible to maintain quality, to increase productivity, and to reduce cost.

Example 2

A second example according to the present invention controls a whole pharmaceutical preparation process using the inspection apparatus of the first example. According to the inspection apparatus and method of pharmaceutical preparations according to the present invention, it is possible to perform an inspection of almost all specimens nondestructively and in real time, and to inspect information, including average components of a plurality of specimens of the same kind or a homogeneous specimen, and the like. Therefore, it is possible to respond to a change like a drift under manufacturing, and the like with high accuracy.

Figure 6:
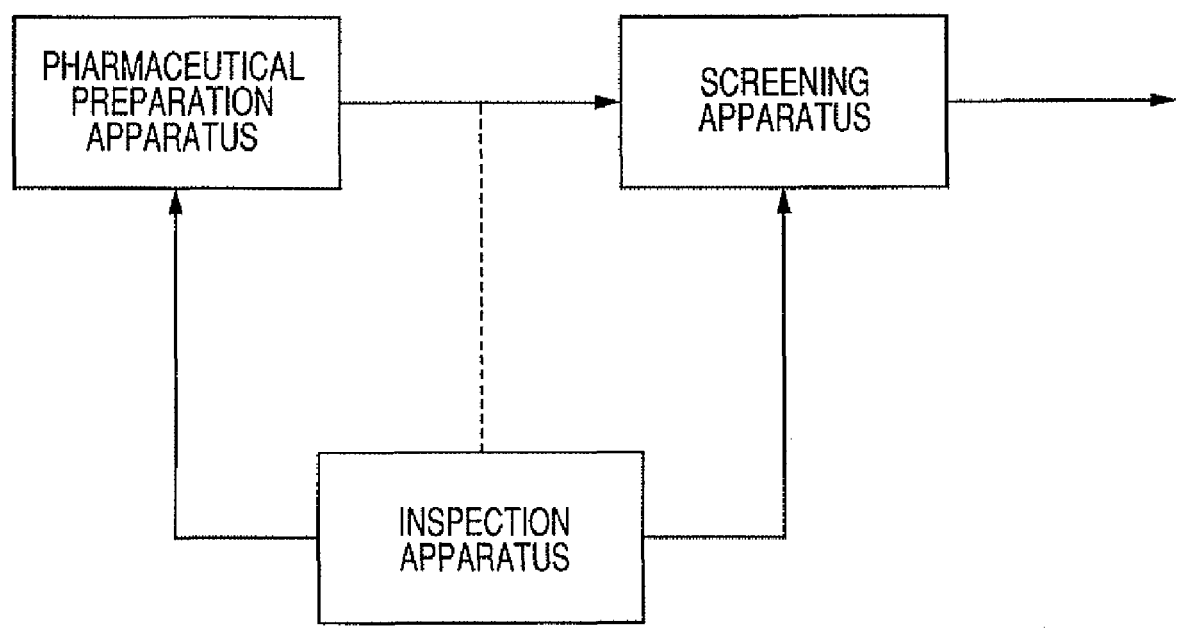
FIG. 6 is a block diagram illustrating a pharmaceutical preparation process control method of a second example according to the present invention.

FIG. 6 is a block diagram of a system which manages a manufacturing process using an inspection apparatus. This system inspects many tablets or the like, which are manufactured by a pharmaceutical preparation apparatus and move from there, by the inspection apparatus of the present invention, and discards a part of tablets by a screening apparatus when a test result is out of a standard value range and the part of tablets are rejected. On the same time, this system performs control of returning the pharmaceutical preparation apparatus to a normal state so that a test result may become within the standard value range, by feeding back to manufacturing parameters (a blending ratio of components, manufacturing temperature, agitating strength within a chamber, and the like) of the pharmaceutical preparation apparatus.

Such a system corresponds to Process Analytical Technology (PAT) which will become important in drug manufacturing from now on. In addition, since such a system observes a state nondestructively in real time, it is possible not only to manufacture pharmaceutical preparations in always good conditions, but also to reduce extremely what are discarded because of disqualification. Therefore, it is possible to reduce manufacturing cost remarkably.

Example 3

Depending on an application to which it is used, a solid state laser type described in the embodiments and examples mentioned above may affect apparatus performance by a degree of stability and long term deterioration of an electromagnetic wave oscillation light output. Then, a third example according to the present invention introduces a beam for terahertz wave excitation with a fiber. Whole structure is almost the same as that of the first example as illustrated in FIG. 7, but a femtosecond laser 50 is a fiber laser types and an optical output is supplied by an optical fiber 51.

The optical output is divided into two by an optical branching coupler 52. One of them is introduced by the optical fiber 54 into a terahertz conversion part 55 that the same photoconductive device and optical system as those in FIG. 1 are modularized into one, and generates a terahertz wave 57.

Figure 7:
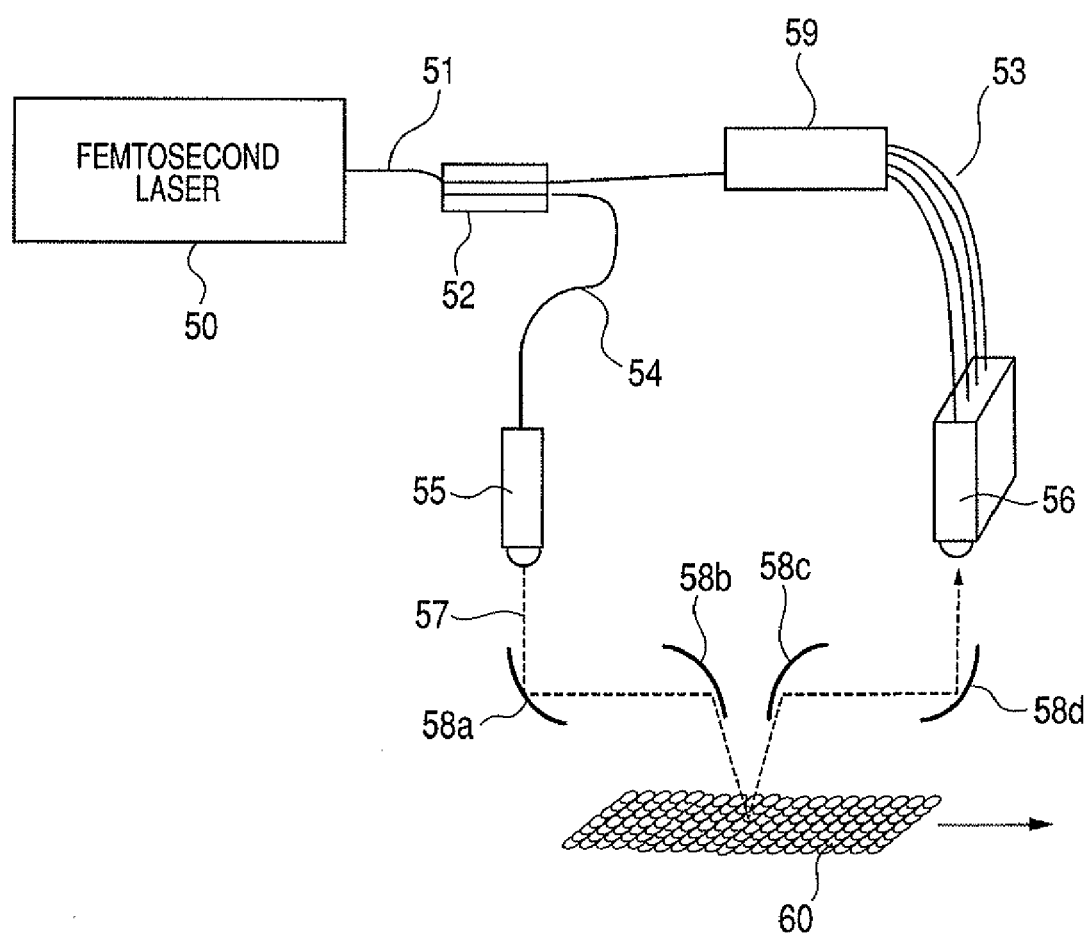
FIG. 7 is a schematic diagram illustrating an inspection apparatus and method relating to a third example according to the present invention.

Although doted lines illustrate a propagation path of the terahertz wave 57 in FIG. 7, in fact, the terahertz wave 57 is formed into the same broad flat beam as that in FIG. 1 to be irradiated on a specimen 60. This terahertz wave flat beam is irradiated on the specimen 60 by parabolic mirrors 58*a* and 58*b*, and a subsequent reflected beam is introduced to a photoconductive device array module 56 by parabolic mirrors 58*c* and 58*d* to be detected there. A detection side has the same constitution as that in FIG. 1. That is, another side of beam divided into two by the optical branching coupler 52 is branched using a 1-to-10 star coupler 59 so that beams having different delay time (detection time) may be irradiated on respective arrayed photoconductive elements. The beams after being branched are incident into respective photoconductive elements after delay time is adjusted respectively with lengths of a fiber 53.

As mentioned above, in an apparatus using photoconductive elements, an excitation wavelength 800-nm band is preferably used as a pump beam. Nevertheless, the pump beam is not limited to this, but it is also good to use a pump beam in a 1550-nm band in which an output of a fiber laser is high. When using the beam in the 1550-nm band, low-temperature growth indium gallium arsenide (LT-InGaAs) is used as the photoconductive element. Nevertheless, the LT-GaAs photoconductive elements may be used by generating a second harmonic wave of the 1550-nm wave with a nonlinear crystal in a second-harmonic generator (SHG).

When a fiber laser is used like this example, it is possible to make constitution very compact, and furthermore, it is possible to make a complicated optical system unnecessary. Other points are the same as those in the first example.

Example 4

Unlike the above-mentioned examples, a fourth example of the present invention has a plurality of detection units so as to detect an electromagnetic wave from different sites of an inspection object in different detection frequencies respectively. Therefore, in the fourth example, oscillation light sources (quantum cascade laser, resonant tunneling diode, and the like) with a plurality of single frequencies which have different oscillating frequencies in are arranged as illustrated in FIG. 8, and each detector (detection unit) detects individually a transmitting terahertz wave of each oscillation light source. FIG. 8 illustrates lenses 80 to condense a terahertz wave to each detector and parabolic mirrors 82 for irradiating a terahertz wave generated by each oscillator on a specimen 81.

In the case of this example, it is not possible to acquire an optical spectrum, but it is possible to do the followings. It is possible to arrange light sources with a plurality of frequencies required for discrimination among the fingerprint spectra of drugs discretely, and to discriminate normality or abnormality of the specimen 81 with transmission intensity ratios of respective frequencies. Here, the specimen 81 which forms an inspection object is a plurality of specimens of the same kind or a homogeneous specimen. Hence, respective detectors detect an electromagnetic wave from the different specimens of the same kind, or an electromagnetic wave from the different sites of the homogeneous specimen, and can acquire information, including the average character and the like of the specimens) based on respective detection signals.

As the oscillator, as mentioned above, there are a quantum cascade laser (QCL), a resonant tunneling diode, a Gunn diode, and the like, and it is good to prepare the oscillator according to a frequency band. For example, the QCL can supply an electromagnetic wave in 1 THz to 4 THz, the RTD can do an electromagnetic wave in 0.3 THz to 2 THz, and the Gunn diode can do an electromagnetic wave in 0.1 THz to about 1 THz, also including harmonics.

In the case of cimetidine described in the description of the first example, when oscillators with oscillating frequencies, such as 0.98 THz, 1.17 THz, 1.73 THz, and 2.17 THz, are prepared and specimen transmission intensity ratios are calculated in respective frequencies, it is possible to discriminate a shift from the standard state of the specimen.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2007-224940, filed Aug. 31, 2007, which is hereby incorporated by reference herein in its entirety.

What is claimed is:

1. An inspection apparatus for performing an inspection using a terahertz wave, comprising:
   an electromagnetic wave generation and irradiation unit which generates a terahertz wave and irradiates the terahertz wave on an inspection object; and
   an electromagnetic wave detection unit having a plurality of detection units,
   wherein the plurality of detection units is arranged so as to detect the terahertz wave which is irradiated by the electromagnetic wave generation and irradiation unit and is transmitted or reflected by interacting with different sites of the inspection object, and is constructed so as to detect the terahertz wave from the different sites in different detection times to acquire a time waveform of the terahertz wave from the inspection object by synthesizing measured values from the plurality of detection units.

2. The inspection apparatus according to claim 1, wherein the terahertz wave is a pulse which includes a portion of frequencies in a frequency domain of 30 GHz to 30 THz and the terahertz wave is irradiated on the different sites of the inspection object respectively; and
   wherein average terahertz wave spectral information of the inspection object is acquired by synthesizing measured values of the transmitted or reflected terahertz wave which is detected by the plurality of detection units.

3. The inspection apparatus according to claim 1, further comprising:
   a plurality of minors; and
   a laser for irradiating light on the electromagnetic wave detection unit via the plurality of minors and on the electromagnetic wave generation and irradiation unit, wherein average terahertz wave spectral information of the inspection object is acquired by synthesizing measured values of the transmitted or reflected terahertz wave which is detected by the plurality of detection units which are irradiated by the light reflected by the plurality of mirrors.

4. The inspection apparatus according to claim 1, further comprising:
   a plurality of fibers which differ in length; and
   a fiber laser for irradiating light on the electromagnetic wave detection unit via the plurality of fibers and on the electromagnetic wave generation and irradiation unit, wherein average terahertz wave spectral information of the inspection object is acquired by synthesizing measured values of the transmitted or reflected terahertz wave which are detected by the plurality of detection units which is irradiated by light through the plurality of fibers.

5. An inspection method for performing an inspection using a terahertz wave, comprising:
   a step of generating a terahertz wave and irradiating the terahertz wave on different sites of an inspection object;
   a step of detecting the terahertz wave, which is transmitted or reflected by interacting with the different sites of the inspection object, by a plurality of detection units in different detection times; and
   a step of acquiring a time waveform of the terahertz wave from the inspection object by synthesizing measured values from the plurality of detection units.

6. The inspection method according to claim 5, wherein the inspection object is an object constructed by a plurality of specimens of the same kind being arranged, or by a homogeneous specimen.

7. The inspection method according to claim 5, wherein the inspection object moves, and different sites of the inspection object change sequentially as the inspection object moves.

8. The inspection method according to claim 5, further comprising:
   a step of screening a specimen when the time waveform of the acquired terahertz wave is out of a reference value range which a homogeneous specimen or specimens of the same kind should fulfill.

9. The inspection method according to claim 5, further comprising:
   a step of performing feedback control of manufacturing conditions of a production apparatus of a specimen so as to be adjusted in a reference value range when the time waveform of the acquired terahertz wave is out of a reference value range which a homogeneous specimen or specimens of the same kind should fulfill.

10. An inspection apparatus for performing an inspection using a terahertz wave, comprising:
    a plurality of generation units for generating a terahertz wave; and
    a plurality of detection units for detecting the terahertz wave which is generated by the plurality of generation units and is transmitted or reflected by an inspection object,
    wherein the plurality of detection units is arranged so as to detect the transmitted or reflected terahertz wave with different delay times respectively, and a time waveform of the transmitted or reflected terahertz wave is acquired by synthesizing measured values from the plurality of detection units.

11. The inspection apparatus according to claim 10, wherein the plurality of generation units and the plurality of detection units are a plurality of photoconductive elements arranged in the shape of a one dimensional array, and a laser beam in a rectangular shape is irradiated on the plurality of photoconductive elements simultaneously, and is condensed in a line.

12. An inspection apparatus for performing an inspection using a terahertz wave, comprising:
    an electromagnetic wave generation and irradiation unit which generates a terahertz wave and irradiates the terahertz wave on an inspection object; and
    an electromagnetic wave detection unit having a plurality of detection units,
    wherein the plurality of detection units is arranged so as to detect the terahertz wave which is irradiated by the electromagnetic wave generation and irradiation unit and is transmitted or reflected by interacting with different sites of the inspection object, and is constructed so as to detect the terahertz wave from the different sites in different detection times or detection frequencies respectively to acquire terahertz wave response information from the inspection object based on detection signals from the plurality of detection units,
    wherein the terahertz wave includes a plurality of frequencies in a frequency domain of 30 GHz to 30 THz and the plurality of frequencies is irradiated on the different sites of the inspection object respectively, and
    wherein respective transmission intensity ratios of the plurality of frequencies are acquired.

13. An inspection method for performing an inspection using a terahertz wave, comprising:
    a step of generating a terahertz wave and irradiating the terahertz wave on different sites of an inspection object;
    a step of detecting the terahertz wave, which is transmitted or reflected by interacting with the different sites of the inspection object, by a plurality of detection units in different detection times or detection frequencies, respectively;

a step of acquiring terahertz wave response information from the inspection object based on detection signals from the plurality of detection units; and a step of screening a specimen when the acquired terahertz wave response information is out of a reference value range which a homogeneous specimen or specimens of the same kind should fulfill.

14. An inspection method for performing an inspection using a terahertz wave, comprising:

a step of generating a terahertz wave and irradiating the terahertz wave on different sites of an inspection object;

a step of detecting the terahertz wave, which is transmitted or reflected by interacting with the different sites of the inspection object, by a plurality of detection units in different detection times or detection frequencies, respectively;

a step of acquiring terahertz wave response information from the inspection object based on detection signals from the plurality of detection units; and a step of performing feedback control of manufacturing conditions of a production apparatus of a specimen so as to be adjusted in a reference value range when the acquired terahertz wave response information is out of a reference value range which a homogeneous specimen or specimens of the same kind should fulfill.

* * * * *